US00PP20044P2

(12) United States Plant Patent
Hart

(10) Patent No.: US PP20,044 P2
(45) Date of Patent: Jun. 2, 2009

(54) ***HELIANTHEMUM* PLANT NAMED 'HARTSWOOD'**

(50) Latin Name: *Helianthemum hybrida*
Varietal Denomination: Hartswood

(76) Inventor: Michael Hart, Woodland Cottage Nursery, Habberley Road, Bewdley, Worcs DY12 1LA (GB)

( * ) Notice: Subject to any disclaimer, the term of this patent is extended or adjusted under 35 U.S.C. 154(b) by 0 days.

(21) Appl. No.: 12/006,216

(22) Filed: Dec. 31, 2007

(51) Int. Cl.
*A01H 5/00* (2006.01)

(52) U.S. Cl. ..... Plt./226

(58) Field of Classification Search ..... Plt./226
See application file for complete search history.

(56) References Cited

PUBLICATIONS

UPOVROM GTITM, Plant Variety Database, European Community PBR 20061999 published Dec. 15, 2006, citation for 'Hartswood'.*

* cited by examiner

*Primary Examiner*—Annette H Para
*Assistant Examiner*—Louanne C Krawczewicz Myers
(74) *Attorney, Agent, or Firm*—C. A. Whealy

(57) ABSTRACT

A new and distinct cultivar of *Helianthemum* plant named 'Hartswood', characterized by its upright to arching plant habit; freely flowering habit; and red purple-colored flowers.

1 Drawing Sheet

Botanical designation: *Helianthemum hybrida.*
Cultivar denomination: 'Hartswood'.

BACKGROUND OF THE INVENTION

The present invention relates to a new and distinct cultivar of *Helianthemum,* botanically known as *Helianthemum hybrida* and hereinafter referred to by the name 'Hartswood'.

The new *Helianthemum* is a naturally-occurring whole plant mutation of an unnamed selection of *Helianthemum hybrida,* not patented. The new *Helianthemum* was discovered and selected by the Inventor as a single flowering plant within a population of plants of the unnamed *Helianthemum* selection in a controlled environment in Bewdley, Worcester, United Kingdom during the summer of 1992.

Asexual reproduction of the new *Helianthemum* by tip cuttings in a controlled environment in Bewdley, Worcester, United Kingdom since July, 1992, has shown that the unique features of this new *Helianthemum* are stable and reproduced true to type in successive generations.

SUMMARY OF THE INVENTION

The cultivar Hartswood has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Hartswood'. These characteristics in combination distinguish 'Hartswood' as a new and distinct cultivar of *Helianthemum:*

1. Upright to arching plant habit.
2. Freely flowering habit.
3. Red purple-colored flowers.

Plants of the new *Helianthemum* can be compared to plants of the parent selection. Plants of the new *Helianthemum* differ from plants of the parent selection primarily in flower color as plants of the parent selection have lighter colored flowers.

Plants of the new *Helianthemum* can also be compared to plants of the cultivar Ben Ledi, not patented. In side-by-side comparisons conducted in Bewdley, Worcester, United Kingdom, plants of the new *Helianthemum* and the cultivar Ben Ledi differed primarily in flower color as plants of the cultivar Ben Ledi had lighter colored flowers.

BRIEF DESCRIPTION OF THE PHOTOGRAPHS

The accompanying colored photographs illustrate the overall appearance of the new *Helianthemum,* showing the colors as true as it is reasonably possible to obtain in colored reproductions of this type. Colors in the photographs may differ slightly from the color values cited in the detailed botanical description which accurately describe the colors of the new *Helianthemum.*

The photograph at the bottom of the sheet comprises a side perspective view of a typical flowering plant of 'Hartswood' grown in a 10 cm. container.

The photograph at the top of the sheet is a close-up view of a typical flower of 'Hartswood'.

DETAILED BOTANICAL DESCRIPTION

The aforementioned photographs and following observations, measurements and values describe plants grown in Lancaster, Pa., under commercial practice during the winter and spring in a polycarbonate-covered greenhouse with day temperatures ranging from 18° C. to 27° C. and night temperatures ranging from 16° C. to 18° C. Plants had been growing for about eight months when the photographs and description were taken. In the following description, color references are made to The Royal Horticultural Society Colour Chart, 1995 Edition, except where general terms of ordinary dictionary significance are used.

Botanical classification: *Helianthemum hybrida* cultivar Hartswood.

Parentage: Naturally-occurring whole plant mutation of an unnamed selection of *Helianthemum hybrida,* not patented.

Propagation:

*Type.*—By tip cuttings.

*Time to initiate roots.*—About 15 days at 22° C.

*Time to produce a rooted young plant, summer.*—About 35 days at 22° C.

*Root description.*—Fibrous.

Plant description:

*Plant and growth habit.*—Perennial; upright to arching plant habit; loose and open plant canopy. Moderately vigorous growth habit. Freely branching habit with about seven to eight lateral branches developing per plant.

*Plant height.*—About 21 cm.

*Plant diameter.*—About 12.5 cm.

*Lateral branch description.*—Length: About 19 cm. Diameter: About 2 mm. Internode length: About 0.6 cm to 2.3 cm. Texture: Pubescent. Strength: Moderately strong. Color: 148B; becoming more grey than 177A with development.

Foliage description:

*Arrangement.*—Opposite, simple.

*Length.*—About 4 cm.

*Width.*—About 9 cm.

*Shape.*—Narrowly elliptic.

*Apex.*—Acute.

*Base.*—Obtuse.

*Margin.*—Entire.

*Texture, upper and lower surfaces.*—Sparsely pubescent.

*Venation pattern.*—Pinnate.

*Color.*—Developing foliage, upper surface: Close to 146A. Developing foliage, lower surface: Close to 146B. Fully expanded foliage, upper surface: Close to 147A; venation, 147B. Fully expanded foliage, lower surface: Close to 147B; venation, 147B.

*Petiole.*—Length: About 3 mm. Diameter: About 1 mm. Texture, upper and lower surfaces: Pubescent. Color, upper and lower surfaces: Close to 146D.

Flower description:

*Flower arrangement and habit.*—Single rose-like flowers arranged in terminal and axillary racemes. Freely flowering habit with seven to nine flowers and flower buds per inflorescence. Flowers face outward to drooping. Flowers not fragrant.

*Natural flowering season.*—Plants of the new *Helianthemum* flower in the mid to late spring in Pennsylvania. Individual flowers last about three days on the plant; flowers persistent.

*Inflorescence height.*—About 10.5 cm.

*Inflorescence diameter.*—About 3.7 cm.

*Flower diameter.*—About 2.8 cm.

*Flower length* (*depth*).—About 1 cm.

*Flower bud.*—Shape: Ovoid. Length: About 9 mm. Diameter: About 7 mm. Color: Close to 186B.

*Petals.*—Quantity/arrangement: About five arranged in a single whorl, radially symmetrical. Length: About 1.3 cm. Width: About 1.5 cm. Shape: Broadly obovate. Apex: Rounded with shallow indentations. Base: Acute. Margin: Entire; sinuate. Texture, upper and lower surfaces: Glabrous, smooth; crinkled. Color: When opening, upper surface: Close to 61A. When opening, lower surface: Close to 185C. Fully opened, upper surface: Towards the apex, close to 185D; center, close to 61B; towards the base, close to 171B. Color towards the apex becoming closer to 75B with development. Fully opened, lower surface: Close to 185D; color becoming closer to 75B to 75C with development.

*Sepals.*—Quantity/arrangement: About three arranged in a single whorl. Length: About 8 mm. Width: About 5 mm. Shape: Elliptical. Apex: Acute. Base: Truncate. Margin: Entire. Texture, upper surface: Glabrous, smooth. Texture, lower surface: Pubescent. Color, upper surface: 146B. Color, lower surface: 148B.

*Peduncles.*—Length: About 5 cm to 7.5 cm. Diameter: About 1 mm. Aspect: Upright to drooping with the weight of the flowers. Texture: Pubescent. Strength: Moderately strong. Color: 148B.

*Pedicels.*—Length: About 1.4 cm. Diameter: Less than 1 mm. Aspect: About 45° from vertical. Texture: Pubescent. Strength: Moderately strong. Color: 148D.

*Reproductive organs.*—Androecium: Stamen number per flower: About 40. Filament length: About 3 mm. Filament diameter: Less than 1 mm. Filament color: Close to 13A. Anther shape: Round. Anther length: About 1 mm. Anther color: 14A. Amount of pollen: Scarce. Pollen color: 14A. Gynoecium: Pistil number per flower: One. Pistil length: About 7 mm. Stigma shape: Rounded. Stigma color: 154A. Style length: About 3 mm. Style color: Close to 150A. Ovary color: Close to 145B. Seed/fruit: Seed and fruit development have not been observed on plants of the new *Helianthemum*.

Garden performance: Plants of the new *Helianthemum* have been observed to have good garden performance and to tolerate temperatures from about −5° C. to about 30° C.

Pathogen/pest resistance: Plants of the new *Helianthemum* have not been observed to be resistant to pests and pathogens common to *Helianthemum.*

It is claimed:

1. A new and distinct *Helianthemum* plant named 'Hartswood' as illustrated and described.

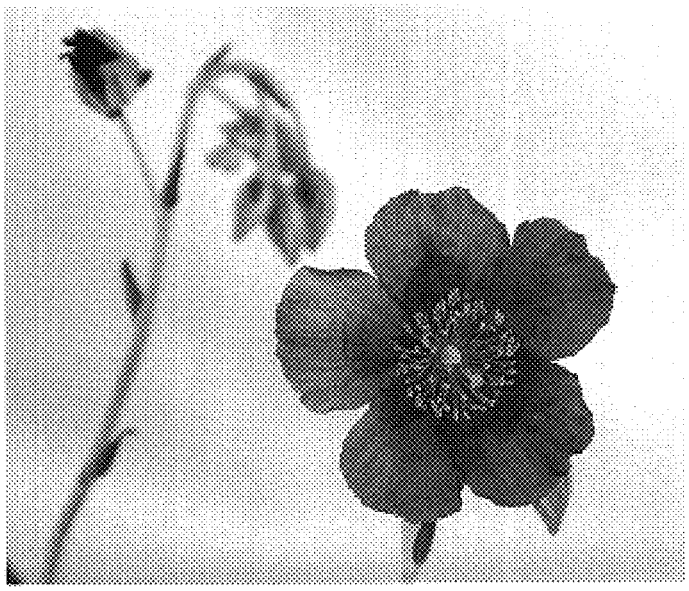
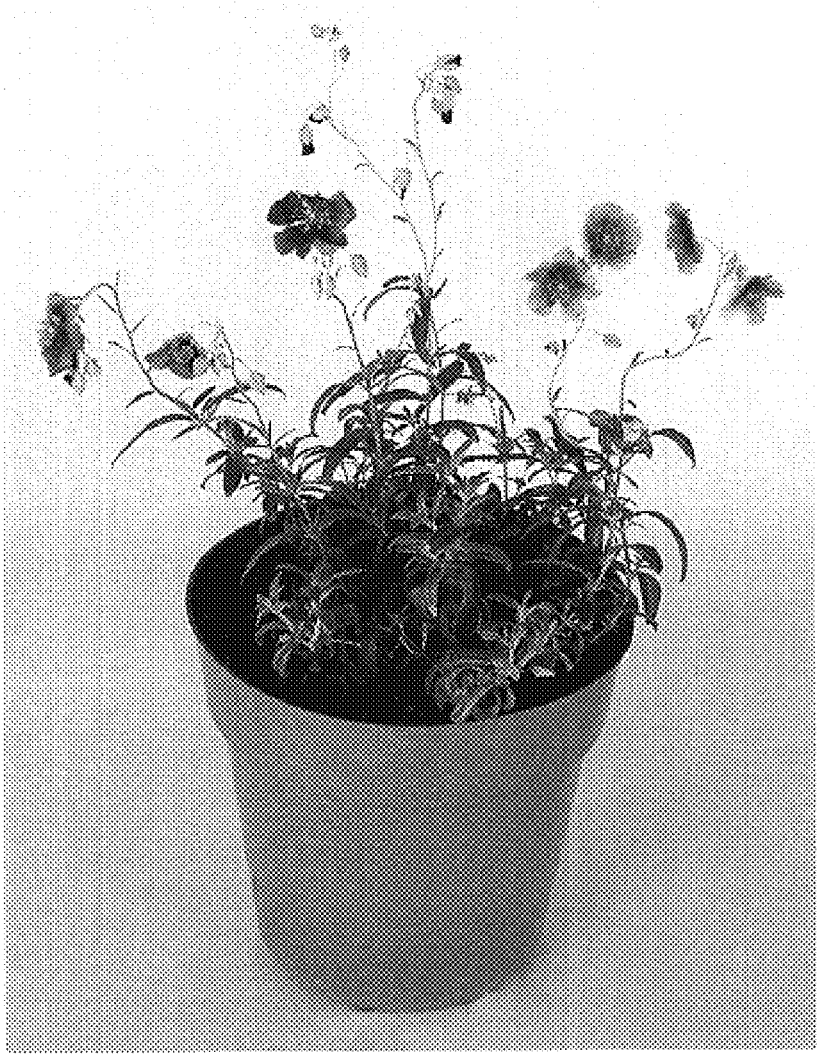

* * * * *